United States Patent [19]

Kajiyama et al.

[11] Patent Number: 5,182,202
[45] Date of Patent: Jan. 26, 1993

[54] **PURIFIED LUCIFERASE FROM *LUCIOLA CRUCIATA***

[75] Inventors: Naoki Kajiyama, Noda; Tsutomu Masuda, Needham, Mass.; Hiroki Tatsumi, Noda; Eiichi Nakano, Iwatsuki, both of Japan

[73] Assignee: Kikkoman Corporation, Noda, Japan

[21] Appl. No.: 742,477

[22] Filed: Aug. 5, 1991

Related U.S. Application Data

[63] Continuation of Ser. No. 274,861, Nov. 22, 1988, abandoned.

[30] Foreign Application Priority Data

Nov. 30, 1987 [JP] Japan .................. 62-300022

[51] Int. Cl.$^5$ .................. C12N 9/02; C12Q 1/66
[52] U.S. Cl. .................. 435/189; 435/8
[58] Field of Search .................. 435/189

[56] References Cited

U.S. PATENT DOCUMENTS

| | | | |
|---|---|---|---|
| 4,581,335 | 4/1986 | Baldwin | 435/172.3 |
| 4,968,613 | 11/1990 | Masuda et al. | 435/189 |

FOREIGN PATENT DOCUMENTS

| | | | |
|---|---|---|---|
| 273889 | 7/1988 | European Pat. Off. | |
| 0301541A2 | 2/1989 | European Pat. Off. | |
| 318915 | 6/1989 | European Pat. Off. | 435/189 |
| WO87/03304 | 6/1987 | PCT Int'l Appl. | |
| WO88/00617 | 1/1988 | PCT Int'l Appl. | |

OTHER PUBLICATIONS

DeLuca, Advances in Enzymology, 44, 1976, pp. 37-68, "Firefly Luciferose".
Berezin et al., Bioorg. Khim 3(12), 1589-1604, 1977.
Shimomura et al., Proc. Natl. Acad. Sci., 74(7), 1977, pp. 2799-2802.
Filippova et al., Biochemistry, 44, pp. 1508-1513, 1979.
Esaki, et al., Iconographia Insectorum Japonicorum, 1st ed., Hokuryukan, Tokyo, Japan, 1932.
Methods in Enzymology, 133:3-15 (1986), De Wet et al.
Kricka et al. (1982) *Arch. Biochem. Biophys.*, 217:674-681.
Wienhausen et al. (1985), *Photochem. Photobiol.*, 42:609-611.
Chem. Abs. 69(15):59203w (1968).
Chem. Abs. 110(13):109122g (1989).
N. N. Ugarova et al., Enzyme Microb. Technol., vol. 4, pp. 224-228, "Immobilization of luciferase from the firefly Luciola mingrelica—catalytic properties and stability of the immobilized enzyme" (Jul. 1982).
J. R. De Wet et al., Mol. Cell. Biol., vol. 7, No. 2, pp. 725-737, "Firefly Luciferase Gene: Structure and Expression in Mammalian Cells" (Feb. 1987).
J. R. De Wet et al., Proc., Natl. Acad. Sci. USA, vol. 88, No. 23, pp. 7870-7073, "Cloning of Firefly Luciferase cDNA and the Expression of Active Luciferase in *Escherichia coli*" (Dec. 1985).

*Primary Examiner*—David M. Naff
*Assistant Examiner*—Mike Meller
*Attorney, Agent, or Firm*—Banner, Birch, McKie & Beckett

[57] ABSTRACT

Disclosed is a purified luciferase and a method for making it. The luciferase is obtained from Luciola cruciata. The luciferase has a pH range for stabililty of 6.5-9.0 and a optimum pH range of 8.0-9.5. The enzyme does not act on ADP, CTP, UTP and GTP.

1 Claim, 1 Drawing Sheet

PURIFIED LUCIFERASE FROM *LUCIOLA CRUCIATA*

This application is a continuation of application Ser. No. 274,861, filed Nov. 22, 1988, now abandoned.

BACKGROUND OF THE INVENTION

1. Field of the Invention

This invention relates to a luciferase which catalyzes the oxydation of luciferin by an oxygen molecule.

2. Discussion on Related Art Statement

Luciferases are very effectively usable, for example, for quantitating ATP, but luciferase derived from *Luciola cruciata* is unstable, so that its purification separation has heretofore been unsuccessful [Tanpakushitsu Kakusan Koso (Protein, Nucleic Acid, Enzyme) Vol. 32, No. 10. p. 44–59, particularly p. 47 (p. 1234–1249, particularly p. 1237), (1987)].

SUMMARY OF THE INVENTION

The present invention is intended to provide luciferase derived from *Luciola cruciata*.

In consideration of the conditions described above, the present inventors earnestly investigated and consequently succeeded in isolating luciferase in a stable state from the posterior portion of *Luciola cruciata*, whereby the present invention has been accomplished.

The luciferase of this invention has the following physicochemical properties:

① Action

The luciferase is an enzyme which catalyzes the oxidation of luciferin by an oxygen molecule, as shown by the enzymic reaction formula:

Luciferin + ATP + $O_2 \rightarrow$ Oxyluciferin + AMP + Pyrophosphoric acid + $CO_2$ + light ② Optimum pH, and pH range for stability:
The optimum pH is 8.0–9.5.
The pH range for stability is 6.5–9.0.

DETAILED DESCRIPTION OF PREFERRED EMBODIMENT

The present invention is explained below in detail.
Physicochemical properties of the present enzyme are as follows:

① Action
The present enzyme-catalyzes the oxidation of ciferin by an oxygen molecule, as shown by the enzymic reaction formula:

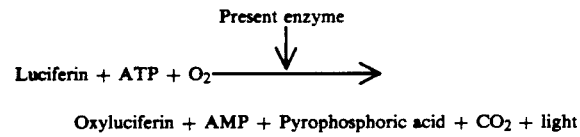

Luciferin + ATP + $O_2$ $\xrightarrow{\text{Present enzyme}}$ Oxyluciferin + AMP + Pyrophosphoric acid + $CO_2$ + light ② Substrate specificity:
The present enzyme does not act on ADP, CTP, UTP and GTP.

② Optimum pH, and pH range for stability

Figure 1:
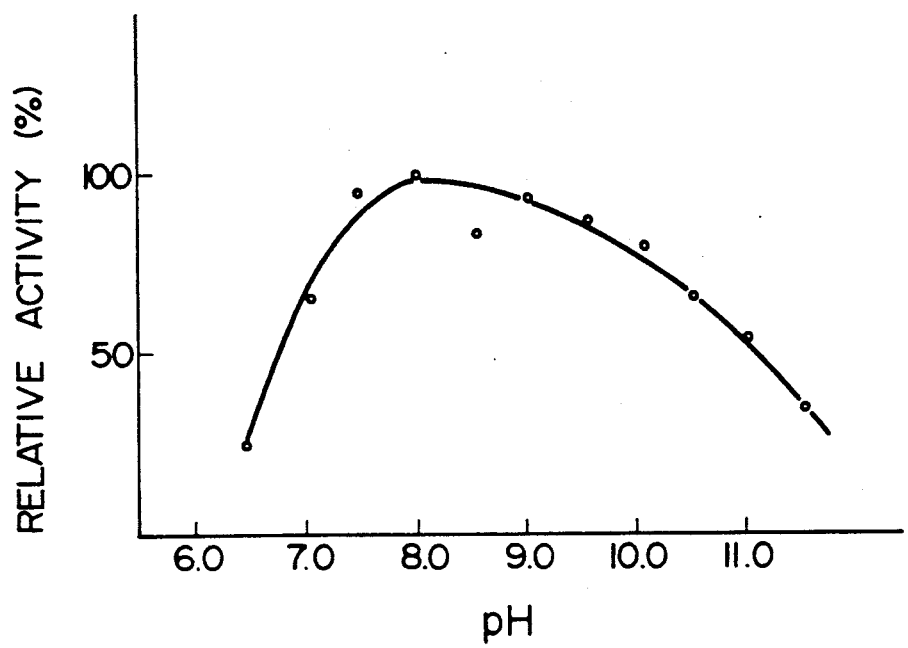
FIG. 1 is a graph showing the optimum pH region of the enzyme of the present invention.
Figure 2:
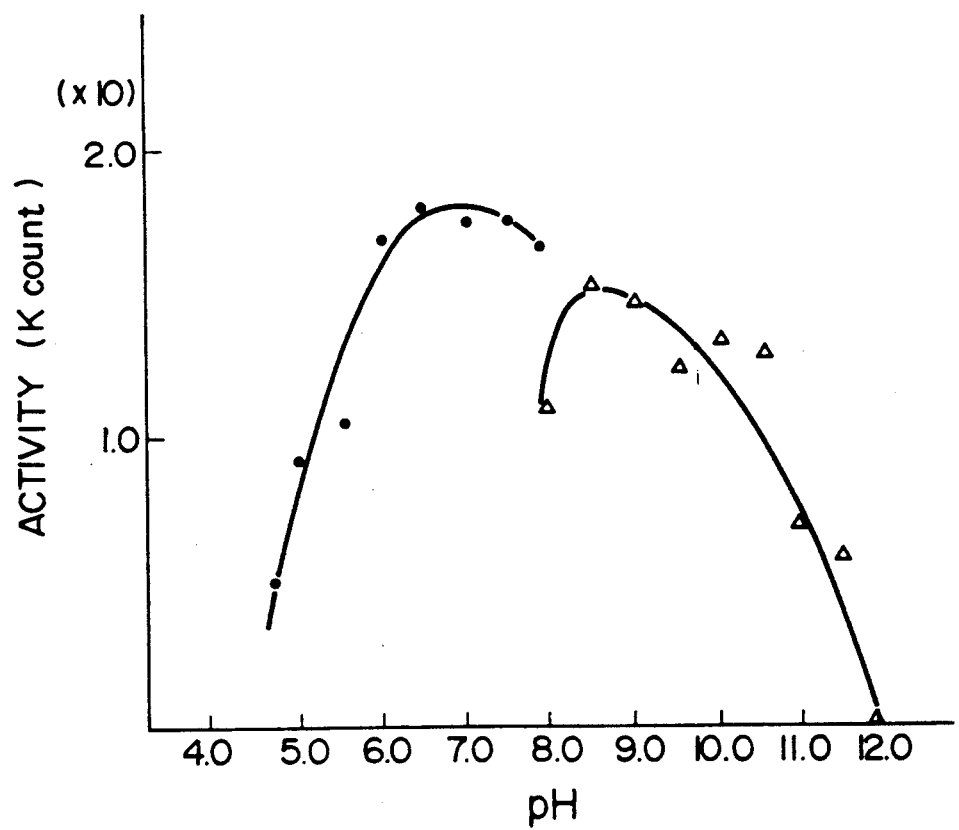
FIG. 2 is a graph showing the pH range for stability of the enzyme of the present invention.

The optimum pH is, as shown in FIG. 1, 8.0–9.5 as measured by carrying out the reaction by the use of luciferin as a substrate at various pH's of 25 mM glycylglycine buffer solution of 6.5 to 11.5 and at a temperature of 30° C., and measuring the quantity of light (the number of photons) emitted in 20 seconds. The pH range for stability is, as shown in FIG. 2, 6.5–9.0 as measured by adding the enzyme to each of buffer solutions [25 mM phosphate buffer solutions (pH 4.6–8.0) and 25 mM glycine.sodium chloride-sodium hydroxide buffer solutions (pH 8.0–11.5), each of which contains ammonium sulfate to 10% saturation] containing luciferin, and allowing the enzyme to act at a temperature of 0° C. for 4 hours. In FIG. 2, 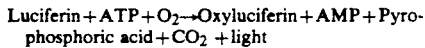 and Δ—Δ show the activity in the case of using the 25 mM phosphate buffer solutions and the activity in the case of using the 25 mM glycine sodium chloride-sodium hydroxide buffer solutions, respectively.

④ Measurement of titer

A luciferin mixed solution is prepared by mixing 8 ml of 25 mM glycylglycine buffer solution (pH 7.8), 0.5 ml of a magnesium sulfate solution [a solution prepared by adding magnesium sulfate to 25 mM glycylglycine buffer solution (pH 7.8) to a magnesium sulfate concentration of 0.1 M] and 0.8 ml of a luciferin solution [a solution prepared by adding luciferin to 25 mM glycylglycine buffer solution (pH 7.8) to a luciferin concentration of 1 mM].

Into a mixture of 400 μl of the luciferin mixed solution thus obtained and 10 μl of luciferase to be assayed is poured 80 μl of an ATP solution [a solution prepared by adding ATP to 25 mM glycylglycine buffer solution (pH 7.8) to an ATP concentration of 10 mM]. Simultaneously with the pouring, the number of photons generated is measured by adding up for 20 seconds by means of a luminometer (LUMINESCENCE READER BLR-201, mfd. by ALOKA CO., LTD.).

⑤ Range of temperature suitable for action

When the reaction is carried out at pH 7.8 and at each temperature and the quantity of light (the number of photons) emitted in 20 seconds, the suitable temperature for action ranges from 0° to 50° C.

⑥ Conditions of inactivation by pH, temperature, etc.
(a) Conditions of inactivation by pH At pH's of 5.0 or lower and 11.0 or higher, the enzyme is completely inactivated after 4 hours.
(b) Conditions of inactivation by temperature At pH 8, the enzyme is completely inactivated by heat treatment at a temperature of 50° C. for 15 minutes.

Next, a concrete means for preparing the present enzyme is described below.

For preparing the present enzyme, any method may be employed. For example, the following method can be exemplified.

As *Luciola cruciata* used in the present invention, there may be used any of that collected from the natural world, that artificially cultivated, etc. This species is distributed in Honshu, Shikoku and Kyushu, Japan. Since a large amount of luciferase exists in the posterior portion of *Luciola cruciata*, said posterior portion is suitable as a source from which luciferase is separated.

*Luciola cruciata* is added to a buffer solution and ground to obtain a ground product.

As the buffer solution, any one can be used so long as it does not inactivate luciferase, and there may be exemplified, for example, solutions prepared by adding ammonium sulfate to each of tris(hydroxy)aminomethane-hydrochloric acid buffer solutions, glycine.sodiumchloride-sodium hydroxide buffer solutions, phosphate buffer solutions, etc. to 10% saturation.

As a means for the grinding, there may be exemplified, for example, a method using a mortar and a pestle, and methods using a homogenizer, a Waring blender, a French press, or the like.

Subsequently, the residue is removed from the ground product by usual centrifugation, filtration or the like to obtain a crude enzyme solution. If necessary, the crude enzyme solution is treated by a method properly selected from freeze-drying, alcohol precipitation, acetone precipitation, etc., to obtain crude enzyme powder.

A purified enzyme preparation can be obtained from the crude enzyme solution or the crude enzyme powder by a combination of methods properly selected from the group consisting of, for example, gel filtration methods using Sephadex, Ultrogel, Bio-Gel, etc.; adsorption-and-elution method using ion exchangers; electrophoretic methods using polyacrylamide gels, etc.; adsorption-and-elution methods using hydroxyapatite; sedimentation methods such as sucrose gradient centrifugation, and the like; affinity chromatographic methods; and fractionation methods using a molecular sieve membrane, a hollow-fiber membrane,, etc.

The present invention is further illustrated with the following example.

To 25 mM tris(hydroxy)aminomethane-hydrochloric acid buffer was added 1 mM disodium ethylenediaminetetraacetate and 2 mM phenylmethylsulfonyl fluoride, followed by adding thereto ammonium sulfate to 10% saturation. To 15 ml of the mixed solution (pH 7.8) thus obtained was added the posterior portions of 150 insects (*Luciola cruciata*) (purchased from Seibu Department Store Co., Ltd.), and destroyed by means of PHYSCO-TRON (mfd. by NITI-ON Medical and Physical Instrument Manufacturing Company LTD.). The liquid thus obtained was centrifuged at 12,000 r.p.m. for 20 minutes to obtain 14.5 ml of a supernatant (a crude enzyme solution).

The crude enzyme solution thus obtained was subjected to salting-out by the use of ammonium sulfate by a conventional method, and the precipitate formed at 30 to 60% saturation was centrifuged at 30,000 r.p.m. for 10 minutes. The resulting precipitate was dissolved in a 25 mM mixed solution [a solution (pH 7.8) prepared by adding 1 mM disodium ethylenediaminetetraacetate and ammonium sulfate in such an amount that 10% saturation therewith was effected, to a small amount of 25 mM tris(hydroxy)aminomethane-hydrochloric acid buffer] to obtain a solution.

Subsequently, this solution was subjected to gel filtration chromatography by passing the same through an Ultrogel AcA34 (mfd. by Pharmacia K.K.) column equilibrated with the above 25 mM mixed solution, to obtain an activity fraction.

The fraction thus obtained was dialyzed against a phosphate buffer solution [a buffer solution prepared by adding 0.1 M sodium chloride and 10% (V/V) of ethylene glycol to a 10 mM sodium hydrogenphosphate-sodium dihydrogenphosphate solution]. The dialyzed solution was adsorbed on a hydroxyapatite HPLC (TSK gel HA-1000, mfd. by Toyo Soda Mfg. Co., Ltd.) column equilibrated with 10 mM phosphate buffer, and linear gradient elution with phosphate buffer solutions (pH 7.5) ranging in concentration from 10 to 100 mM was carried out to obtain 200 μl (enzymic activity: $3.5 \times 10^2$ K count) of a purified luciferase activity fraction derived from *Luciola cruciata*.

What is claimed is:

1. A purified luciferase from *Luciola cruciata* characterized as follows:
   (a) action:
     said purified luciferase is derived from *Luciola cruciata* and catalyzes the oxidation of luciferin by an oxygen molecule, as shown by the enzymatic reaction formula:

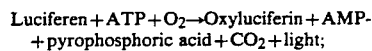
Luciferen + ATP + $O_2 \rightarrow$ Oxyluciferin + AMP- + pyrophosphoric acid + $CO_2$ + light;

(b) optimum pH, and pH range for stability:
     the optimum pH is 8.0 to 9.5, and the pH range for stability is 6.5 to 9.0; and
   (c) substrate specificity:
     the luciferase does not act on ADP, CTP, UTP and GTP;

said purified luciferase having the purity of luciferase purified from *L. cruciata* by:
   dissolving the precipitate formed at 30 to 60% ammonium sulfate saturation from crude L. cruciata luciferase enzyme solution in a solution prepared by adding ethylenediaminetetraacetate to 1mM and ammonium sulfate to 10% to 25mM tris(hydroxy)aminomethane-hydrochloric acid buffer, pH=7.8;
   subjecting said dissolved precipitate solution to gel filtration chromatography and recovering the active fraction;
   dialyzing said active fraction against a buffer solution prepared by adding 0.1 M sodium chloride and 10% (V/V) ethylene glycol to a 10 mM sodium hydrogen phosphate-sodium dihydrogenphosphate solution;
   adsorbing said dialyzed material on a hydroxyapatite column equilibrated with 10 mM phosphate buffer; and
   collecting the fraction having luciferase activity eluted from said hydroxyapatite column by a linear gradient from 10 to 100 mM phosphate buffer, pH=7.5.

* * * * *